US00PP24772P2

(12) United States Plant Patent
Dijkstra

(10) Patent No.: US PP24,772 P2
(45) Date of Patent: Aug. 12, 2014

(54) ***SEDUM* PLANT NAMED 'ELINE'**

(50) Latin Name: ***Sedum* hybrid**
Varietal Denomination: Eline

(71) Applicant: Jan Hendrik Jacob Dijkstra, Oudeschip (NL)

(72) Inventor: Jan Hendrik Jacob Dijkstra, Oudeschip (NL)

( * ) Notice: Subject to any disclaimer, the term of this patent is extended or adjusted under 35 U.S.C. 154(b) by 22 days.

(21) Appl. No.: 13/815,570

(22) Filed: Mar. 11, 2013

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Kent L Bell
(74) *Attorney, Agent, or Firm* — Penny J. Aguirre

(57) ABSTRACT

A new cultivar of *Sedum* plant named 'Eline' that is characterized by its compact plant habit with strong stems that do not flop, its foliage that is dark green to grey-green and strongly tinged with grey-purple, and its flowers that are creamy white to creamy yellow in color.

2 Drawing Sheets

Botanical classification: *Sedum* hybrid.
Variety denomination: 'Eline'.

BACKGROUND OF THE INVENTION

The present invention relates to a new and distinct cultivar of *Sedum* plant of hybrid origin known as *Sedum* 'Eline' and will be referred to hereinafter by its cultivar name, 'Eline'. The new cultivar of *Sedum* is a hardy herbaceous perennial grown for use as a landscape plant.

The Inventor discovered the new cultivar, 'Eline', as a chance seedling in a garden in Oudeschip, The Netherlands in 2009. The parentage is unknown, however there were plants of *Sedum* hybrid cultivars 'Karl Funkelstein', 'Matrona', and 'Purple Emperor', and *S. telephium* 'Atropurpureum' (all unpatented), and unnamed plants of *S. telephium* subsp. *ruprechtii* growing in the same garden and are possible parents.

Asexual propagation of the new cultivar was first accomplished by the Inventor by stem cuttings in September of 2009 in Oudeschip, The Netherlands. Asexual propagation by cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'Eline' as a unique cultivar of *Sedum*.

1. 'Eline' exhibits a compact plant habit with strong stems that do not flop.
2. 'Eline' exhibits foliage that is dark green to grey-green and strongly tinged with grey-purple.
3. 'Eline' exhibits flowers that are creamy white to creamy yellow in color.

'Eline' can be most closely compared to the plant cultivars and variety that are possible parent plants. The unnamed plant of *S. telephium* subsp. *ruprechtii* is similar to 'Eline' in flower color, but differs from 'Eline' in having weaker stems that tend to lodge and in having foliage that is grey-green in color without being tinged with grey-purple. 'Matrona', 'Purple Emperor', and 'Karl Funkelstein' are all similar to 'Eline' in foliage coloration. Both 'Matrona' and 'Purple Emperor' differ from 'Eline' in having flowers that are lilac-pink in color and in having much taller plant heights. 'Karl Funkelstein' is similar to 'Eline' in having purple tinged foliage and in having a compact plant height, but differs from 'Eline' in having flowers that are bright pink in color.

BRIEF DESCRIPTION OF THE DRAWINGS

The accompanying colored photographs illustrate the overall appearance and distinct characteristics of the new *Sedum*. The photographs were taken of a 2 year-old plant of 'Eline' as grown outdoors in a 17-cm container in Boskoop, The Netherlands.

The photograph in FIG. 1 provides a side view of 'Eline' in bloom.

Figure 1:
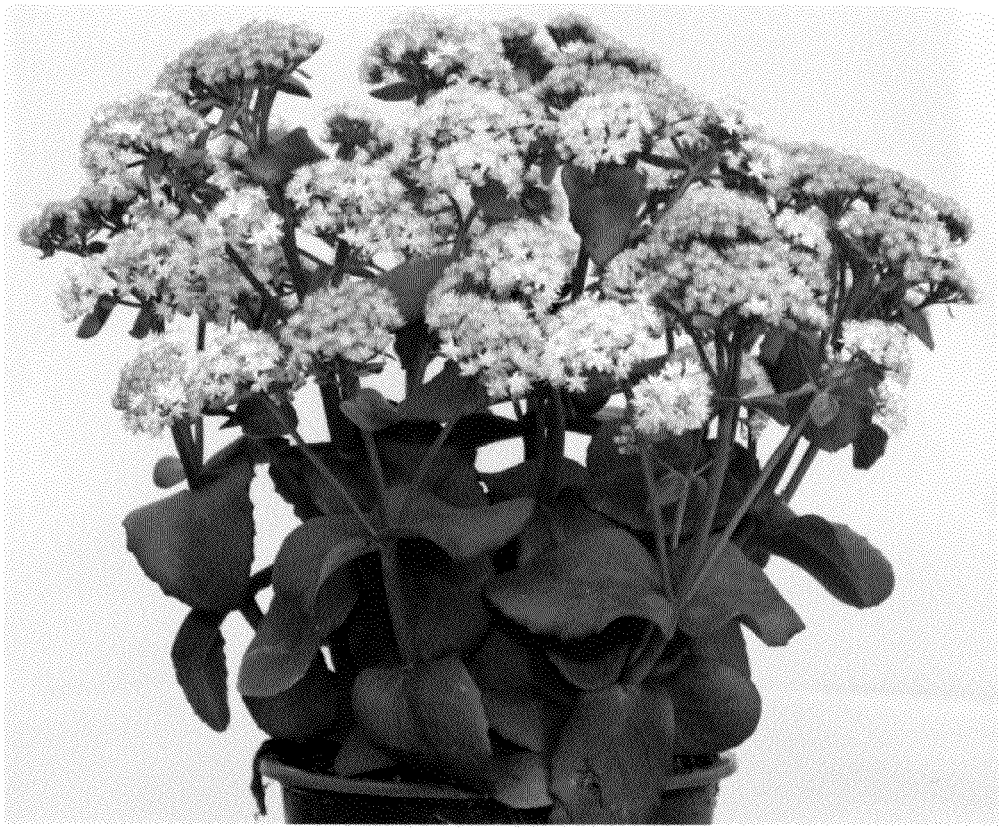
Figure 2:
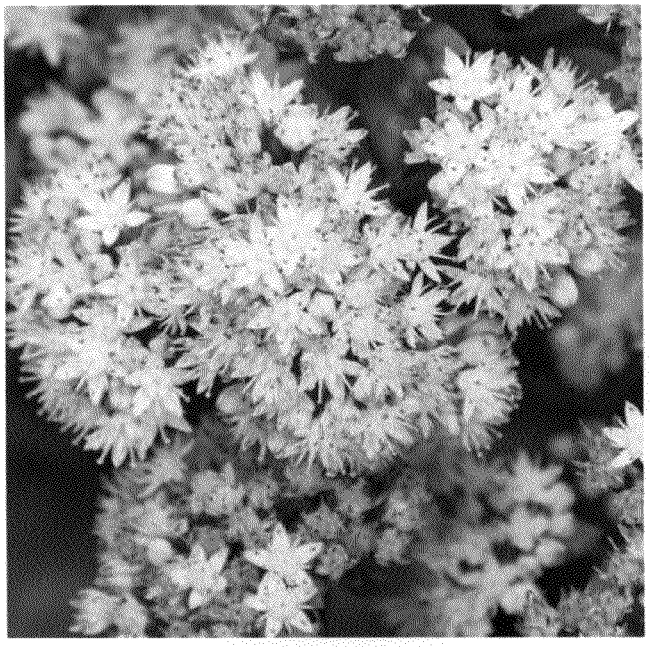

The photograph in FIG. 2 provides a close-up view of inflorescences of 'Eline'.

Figure 3:
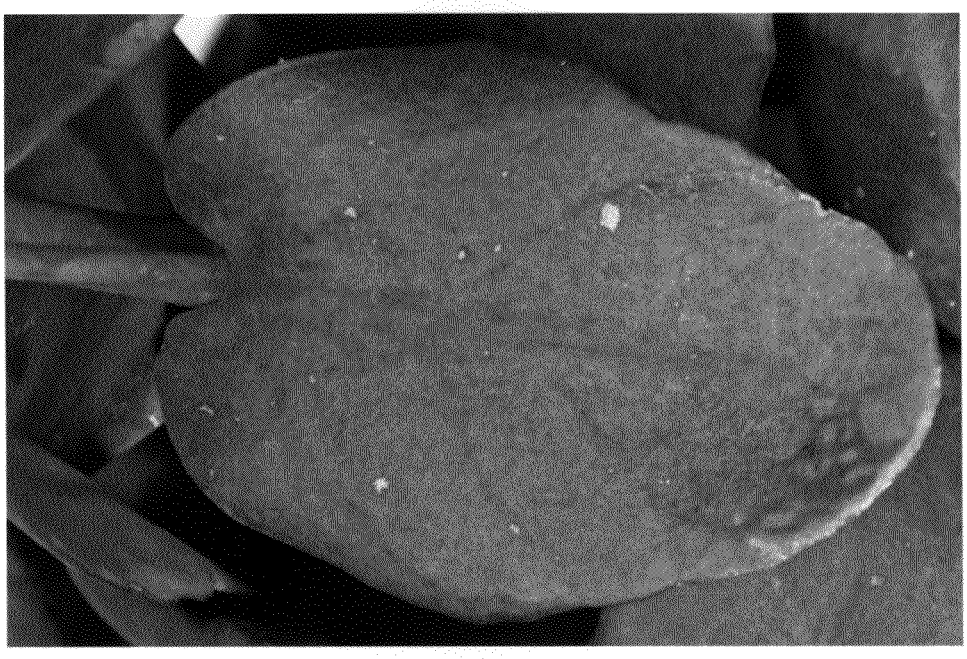

The photograph in FIG. 3 provides a close-up view of a leaf of 'Eline'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 2 year-old plants as grown in 17-cm containers outdoors in Boskoop, The Netherlands. Plants were grown under average day temperatures of 12° C. to 32° C. and average night temperature of 6° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—About 6 weeks in late summer to early autumn in The Netherlands.

*Plant type.*—Herbaceous perennial.

*Plant habit.*—Compact, broadly upright, with flower stems that are held upright and do not flop.

*Height and spread.*—Reaches about 27 cm in height and about 35 cm in spread.

*Cold hardiness.*—At least in U.S.D.A. Zone 5.

*Diseases.*—Plants have been observed to have healthy foliage and disease free, similar to *Sedum* 'Matrona', however no specific disease resistance has been identified.

*Root description.*—Fibrous.

*Propagation.*—Stem cuttings.

*Growth rate.*—Moderate.

Stem description:

*Stem shape.*—Round.

*Stem size.*—Average of 13 cm in length and 6 mm in width.

*Internode length.*—Average of 3 cm.

*Stem color.*—178A, base is 143C.

*Stem surface.*—Moderately glossy.

*Branching habit.*—Moderate basal branching, with an average of 9 lateral branches.

Foliage description:

*Leaf shape.*—Ovate, slightly undulate.

*Leaf division.*—Simple.

*Leaf arrangement.*—Opposite.

*Leaf base.*—Cordate.

*Leaf apex.*—Bluntly acute.

*Leaf venation.*—Pinnate, upper surface color between N186C and 187A, lower surface color; 144A.

*Leaf margins.*—Irregular and undeep dentate.

*Leaf attachment.*—Sessile.

*Leaf texture.*—Succulent.

*Leaf surface.*—Slightly glossy.

*Leaf color.*—Young upper surface; between 137A and N138B, young lower surface; between N138C and 191A, mature upper surface; between N137A and N189A and heavily tinged with a color between N186C and 187A, mature lower surface; between N138B and 191A.

*Leaf size.*—Average of 7 cm in length and 4.9 cm in width.

Flower description:

*Inflorescence type.*—Dense, slightly rounded compound cymes.

*Inflorescence size.*—Average of 10.2 cm in height and 13.2 cm in width.

*Lastingness of inflorescence.*—About 14 days.

*Flower type.*—Rotate.

*Flower number.*—An average of 300 flowers per inflorescence.

*Flower fragrance.*—Faint and sweet.

*Flower buds.*—Elliptic to obovate in shape, about 5 mm length and 2 mm in diameter, color; 157C, tip tinged 160A.

*Flower size.*—About 7 mm in depth and 8 cm in diameter.

*Peduncles.*—Slightly oval in shape, moderately strong, 8.2 cm in length and 3.5 cm in width, 183A to 183B in color with under side strongly tinged with 148D, slightly glossy surface, average angle of main cyme is 0° (=straight upright), average angle of secondary cymes is 40°.

*Pedicels.*—Slightly oval in shape, moderately strong, 2 mm in length and 0.75 mm in diameter, 138B in color, slightly glossy surface, an average angle is 30° (0°=straight upright).

*Sepals.*—5, 1.5 mm in length and 0.8 mm in width, narrow ovate in shape, base fused, upper and lower surfaces 143C in color with tip N186C, entire margin, acute apex, dull and smooth on both surfaces.

*Petals.*—5, rotate, about 5 mm in length and 1 mm in width, ovate in shape, lower 20% fused, acute apex, entire margin, color of inner and outer surfaces when opening; NN155D, tip 158B to 158C, color of inner and outer surfaces when fully opened; NN155D, tip 158C to 158D, dull and smooth on both surfaces.

*Calyx.*—Campanulate in shape, 1.5 mm in length and 3 mm in diameter.

Reproductive organs:

*Pistils.*—5, about 0.7 mm in length, stigma has an acute apex and are NN155C to NN155D in color, style is 0.5 mm in length and NN155C to NN155D in color, ovary is a blend of NN155D to 155A in color and fading to 145B to 145A.

*Stamens.*—10, 5 stamens are placed in the base of petals, other 5 stamens are free, filament is 4.5 mm in length and NN155D in color, anther is basifixed, flattened, broad and oblong, about 0.5 mm in length and between 23C and 33B in color, pollen is very low in quantity and 5B to 5C in color.

*Fruit and seed.*—Seed production was not observed.

It is claimed:

1. A new and distinct variety of *Sedum* plant named 'Eline' as described and illustrated herein.

* * * * *